United States Patent [19]

Yoshida

[11] Patent Number: 5,249,395
[45] Date of Patent: Oct. 5, 1993

[54] METHOD OF POLISHING DENTAL INSTRUMENT

[75] Inventor: Masahiro Yoshida, Hidaka, Japan

[73] Assignee: Hoya Corporation, Tokyo, Japan

[21] Appl. No.: 873,216

[22] Filed: Apr. 24, 1992

[30] Foreign Application Priority Data

Apr. 30, 1991 [JP] Japan ................... 3-124593

[51] Int. Cl.⁵ .................... B24B 31/02; B24B 1/00
[52] U.S. Cl. ........................ 51/316; 51/317; 51/164.5
[58] Field of Search ............ 51/281 R, 313, 317, 51/163.1, 163.2, 164.1, 164.2, 164.5, 7, 17, 316

[56] References Cited

U.S. PATENT DOCUMENTS

| | | | |
|---|---|---|---|
| 2,431,870 | 12/1947 | Huenerfauth et al. | 51/164.5 |
| 2,947,124 | 8/1960 | Madigan et al. | 51/164.5 |
| 3,543,452 | 12/1970 | Guenther | 51/317 |
| 3,684,466 | 8/1972 | Petrone | 51/164.5 |
| 3,997,358 | 12/1976 | Taylor | 51/313 |
| 4,077,808 | 3/1978 | Church et al. | 51/295 |
| 4,964,883 | 10/1990 | Morris et al. | 51/309 |
| 5,011,508 | 4/1991 | Wald et al. | 51/307 |

FOREIGN PATENT DOCUMENTS

| | | | |
|---|---|---|---|
| 2402843 | 8/1974 | Fed. Rep. of Germany | 51/316 |
| 1177966 | 7/1989 | Japan | 51/164.1 |
| 3131469 | 6/1991 | Japan | 51/164.1 |

Primary Examiner—Bruce M. Kisliuk
Assistant Examiner—Bryan S. Reichenbach
Attorney, Agent, or Firm—Nixon & Vanderhye

[57] ABSTRACT

In a method of polishing a dental instrument, the dental instrument made of a ceramic material and having fine irregular portions along a surface thereof is placed in a container, together with a spherical ceramic whose grain size is 30~400 μm, and an abrasive whose grain size is at most equal to 20 μm and a liquid. The container is moved whereby the dental instrument is polished effectively.

13 Claims, 4 Drawing Sheets

100 μm

100 μm

10 μm

100μm

10μm

METHOD OF POLISHING DENTAL INSTRUMENT

BACKGROUND OF THE INVENTION

The present invention relates to a method of polishing a dental instrument and, more particularly, to a method of polishing a dental instrument such as a dental bracket, an artificial dental crown and a dental implant.

Conventionally, a dental instrument which is made of ceramics, such as an artificial dental crown, a dental implant, and a dental bracket generally has a complicated configuration with irregularities. The dental instrument is also small-sized.

Japanese Utility Model Laid-Open No. HEI 2-139617 discloses such a conventional dental bracket. The disclosed dental bracket is made of ceramics in place of a metallic material such as stainless steel or the like, for the purpose of an improvement in aesthetic appreciation. The disclosed dental bracket generally has a configuration as illustrated in FIGS. 8 and 9. The dental bracket 1 is arranged such that a pair of walls 3 and 4 forming a slot 2 is integrally provided continuously in unison over the entire widthwise length in a bracket body 5, and four (4) ligature-wire engaging wings 6~9 are integrally provided in extension or projection on both ends of an outer side surface of each of the slot-forming walls 3 and 4. A dimension of the dental bracket 1 per se is about 2~3.5 mm in width, about 2~3 mm in length, and about 2~3 mm in thickness. A groove width of the slot 2 is about 450~500 $\mu$m and a depth thereof is about 700~900 $\mu$m. As a material of the dental bracket 1, partially stabilized zirconia (e.g. zirconia stabilized with yttria), polymethylmethacrylate, dental composite resin or the like is used. The dental bracket 1 is integrally formed from these materials by injection molding. It is also formed by cast-molding a dental composite resin into a silicon rubber-made mold. Further, the dental bracket 1 may be prepared by subjecting these materials to grinding processing, although it is not so much preferable for the reason to be described later.

In use of the dental bracket 1 arranged as described above, a bottom surface of the bracket body 5 is bonded to and is fixedly mounted on a surface of a tooth; a long and narrow metallic wire (arch wire) 10 having a rectangular cross-sectional configuration passes through the slot 2; and the wire 10 is fixedly mounted on the slot 2 by another long and narrow wire (ligature wire) 11 which is engaged with the ligature-wire engaging wings 6~9. Under this condition, loads such as torsion, bending, tension and the like are applied to the arch wire 10, whereby the loads are transmitted or transferred to the tooth so that movement of the tooth occurs along the arch wire 10.

By the way, an oral cavity is placed under an insanitary environment due to various foods and drinks taken thereinto.

Since the oral cavity is under an insanitary environment as described above, dental plaque is liable to be deposited on the surface of the dental instrument, and various bacteria are liable to be bred or propagated. In case where the surface of the dental instrument is rough, plaque deposition and bacteria breeding are particularly remarkable. Furthermore, if the surface of the dental instrument is rough, there are problems that cracks are liable to be developed, and the strength is reduced. Therefore, it has been desired to solve such problems.

Moreover, the ceramic-made dental bracket 1 generally has a large frictional resistance which occurs between the inner surface of the slot 2 and the surface of the arch wire 10, as compared with a metallic bracket. For this reason, there is also a fundamental problem that an efficiency of moving the tooth is low and a time required for correcting the irregularities of the teeth is long.

Further, the arch wire 10 and the ligature wire 11 causes friction at their contact portions with the bracket 1. In the worst case, there is possibility that the wire 10 and the ligature wire 11 are cut off. These problems are related to a hardness and a surface roughness of the bracket material. In particular, since the ceramic-made bracket has high hardness, the wire and the like are worn at their portions which has been in contact with small irregularities of the dental bracket so that friction becomes larger.

If friction which occurs between the inner surface of the slot and the surface of the wire is so much large, there are problems that the efficiency of moving the tooth is lowered, and a period for the correction of the irregularities of the teeth is lengthened.

For the reason discussed above, it is required that the surface of the slot 2 is finished to a smooth surface with high accuracy, desirably, to a surface equal to or smaller than the maximum height $R_{max}=2$ $\mu$m in B0601 of JIS (Japanese Industrial Standard). In case where a dental bracket made of ceramics is produced, there are used a method in which a dental bracket product is formed by grinding a mother material of ceramics as described above, and a method in which a raw material powder is molded into a predetermined bracket configuration with a mold, and is sintered. In the former method, however, large-sized grinding defects occur. For this reason, even if polishing processing is carried out, it is difficult that the maximum height $R_{max}$ is controlled within an allowable limit. On the other hand, in the latter method, the defects in or on the surface of the mold into which the raw material powder is placed, are transferred to the surface of a dental instrument formed so that surface defects occur on the dental instrument. However, in the latter method, it is possible to maintain these defects smaller than the grinding defects in the former method. And by polishing the surface of the formed dental instrument, it is possible to further reduce the defects. As described previously, however, since the dental bracket of this kind is small-sized, and has also a complicated configuration, it is extremely difficult to polish the surface of the bracket, particularly, the inner surface of the slot.

Conventionally, as a method of polishing a surface of ceramics or the like, there is a polishing method using an acid or the like. However, there is a disadvantage that the polishing method using the acid can be applied to very limited ceramics such as alumina and the like.

Further, as disclosed in Japanese Patent Laid-Open No. HEI 1-177965, there is a method in which a material to be polished is barrel-polished in a mixture including a spherical resin, an abrasive and water. In the polishing method, a glass material or the like is polished with the resin and the abrasive whose grain size is small. Although the polishing method disclosed in the above Japanese patent gazette enables to polish a relatively plain or flat surface and a wide recess, it is not preferable that the disclosed polishing method is directly applied to polishing of the dental bracket 1. The reason for this is that a polishing speed is extremely slow, and clean polishing of an inner surface of a groove is impossible because the spherical resin is clogged in the slot 2 with extremely narrow groove width, within a short time. In view of this, further consideration has been made on this point. As a result, it has been found that the reason why the spherical resin is clogged in the groove is that the spherical resin per se is abraded or worn fastly because it has low hardness so that the configuration thereof becomes irregular. Moreover, it has been found that the reason why the polishing speed is low is due to the fact that, since the spherical resin has a smaller specific gravity than the ceramic-made dental bracket 1 to be polished, the spherical resin floats up to a surface of a polished liquid, and the polishing efficiency is lowered.

SUMMARY OF THE INVENTION

It is therefore an object of the invention to provide a method of polishing a dental instrument which is made of ceramics or a composite material containing ceramics and which has at least one narrow groove or recess, according to which a surface of the dental instrument, particularly fine irregular portions such as narrow grooves or recesses formed thereon can be polished effectively.

According to the invention, there is provided a method of polishing a dental instrument, comprising the steps of:

placing, into a container, the dental instrument and a mixture of a spherical ceramics whose grain size is 30~400 $\mu$m, an abrasive whose grain size is at most equal to 20 $\mu$m and a liquid, said dental instrument being made of any one of ceramics and a composite material containing the ceramics, and having fine irregular portions at the surface thereof; and moving the container thereby polishing the dental instrument.

Preferably, the amount of the abrasive is 1~50% the volume of the spherical ceramics.

Preferably, the narrow groove and recess in the dental instrument has a width of 450~500 $\mu$m, and a depth of 700~900 $\mu$m.

With the above arrangement of the invention, the spherical ceramics has high hardness and is less liable to be abraded or worn so that its configuration can be maintained constant. Further, the spherical ceramics is superior in fluidity when it is mixed with the abrasive. Therefore, the spherical ceramics is not liable to be clogged in the fine irregular portions including narrow grooves or recesses. Further, since having a specific gravity substantially equal to that of the dental instrument, the spherical ceramics does not float up so that the polishing can be performed effectively. Moreover, since having a small grain size such as 30~400 $\mu$m, the spherical ceramics can sufficiently enter into the fine irregular portions including narrow grooves or recesses in the dental instrument.

DESCRIPTION OF THE EMBODIMENTS

Figure 1:
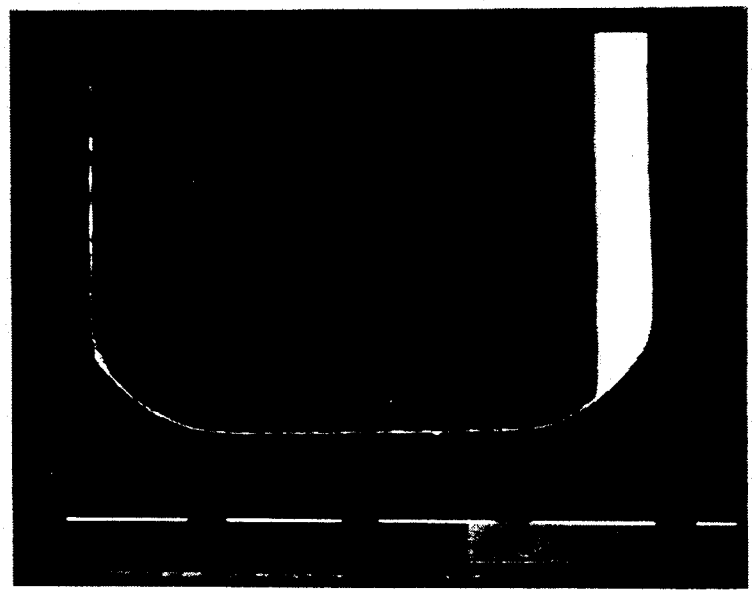
FIG. 1 is a photomicrograph, at a low magnification, showing the bottom of the slot and its neighborhood in a dental bracket after polishing, according to an embodiment 1 of the invention.

A method of polishing a dental instrument, according to the invention, will hereunder be described in detail with reference to the accompanying drawings.

The polishing method according to the invention comprises the steps of:

placing, into a container, the dental instrument and a mixture of a spherical ceramics whose grain size is 30~400 $\mu$m, an abrasive whose grain size is at most equal to 20 $\mu$m and a liquid, said dental instrument being made of any one of ceramics and a composite material containing the ceramics, and having fine irregular portions thereon; and moving the container thereby polishing the dental instrument.

In the polishing method according to the invention, since having a small grain size (30~400 $\mu$m) and a spherical form, the spherical ceramics per se has almost no polishing effect. According to the invention, the abrasive having a small grain size ($\leq$20 $\mu$m) is used together with the spherical ceramics, and they are rubbed with the dental instrument by the movement of the container, to effect the polishing. That is, by using both the spherical ceramics and the abrasive, remarkable polishing effect can be achieved.

Ceramics such as zirconia, silica, alumina, silicon carbide, silicon nitride, and the like can be used as a material of the spherical ceramics or the polishing beads. Particularly, since partially stabilized zirconia (e.g. zirconia stabilized with yttria) has high wear and abrasion resistance and high density, it is preferable as the material of the polishing beads. Other beads made of polymer and the like may be used, but they have inferior wear and abrasion resistance, and also have low polishing effect when used with the abrasive. Thus, these beads are considered as being inadequate. The spherical ceramics is formed substantially into a true sphere. Since the spherical ceramics is required to enter into the fine irregular portions including narrow grooves or recesses in the dental instrument, its grain size is restricted to 30~400 $\mu$m. It is possible to prepare such spherical ceramics by means of the granulation in the liquid or the like. The reason why the grain size of the spherical ceramics is restricted to be equal to or less than 400 $\mu$m is that the spherical ceramics is required to enter into the fine irregular portions including grooves or recesses having a narrow width (e.g. 450 $\mu$m) in the dental instrument. However, if the grain size is smaller than 30 $\mu$m, the polishing speed is extremely and unfavorably reduced, which is the reason why the grain size of the spherical ceramics is restricted to be equal or larger than 30 μm. When such spherical ceramics are used, it is possible to maintain its configuration constant, because its hardness is high and its wear or abrasion resistance is high. Further, when the above-described spherical ceramics is mixed with the abrasive, the ceramics shows superior fluidity. Accordingly, the spherical ceramics is less liable to be clogged in the fine irregular portions such as narrow grooves or recesses. Furthermore, since the spherical ceramics has a specific gravity substantially equal to that of the dental instrument, it does not float up, whereby excellent polishing efficiency can be achieved.

General abrasives made of alumina, zirconia, silicon carbide, silicon nitride, cerium oxide, diamond or the like can be used as the abrasive. The grain size of the abrasive is restricted to be equal to or less than 20 μm. The reason for this is that, if the grain size of the abrasives exceeds 20 μm, the surface of the dental instrument after polished becomes rough so that the desirable polishing effect cannot be realized sufficiently. It is preferable that the grain size of the abrasive is 0.2~5 μm. If the abrasive is added in a smaller amount, the polishing speed is slower, whereas, if the abrasive is added in a larger amount, the spherical ceramics is more liable to be clogged in the fine irregular portions such as narrow grooves or recesses. Although an upper limit of the amount of the abrasive may vary depending upon the kinds or types and grain size of the abrasive, it is approximately 50% based on the volume of the spherical ceramics. If the amount of the abrasive exceeds 50%, movement or motion of the spherical ceramics is lowered, and the polishing speed is unfavorably decreased. Further, if the amount of the abrasive is less than 1%, the polishing speed is also decreased because of a small amount of the abrasive.

Furthermore, in case where the fine irregular portions such as grooves or recesses in the dental instrument are deep, the spherical ceramics is liable to be clogged in the fine irregular portions, if an amount of the abrasive is large. Thus, it is preferable that the amount of the abrasive is 1~15% by volume, particularly, 1~8% based on the volume of the spherical ceramics.

A method of moving the container is not particularly limited. However, it is preferable to use a barrel polishing method. The barrel polishing method is a method in which an article to be polished and abrasive grains are placed in a container, and movement such as rotation, vibration or oscillation, or planetary motion is applied to the container in a wet system (water is usually used) or in a dry system. By application of rotation, vibration or planetary motion to the container, abrasive grains are forcibly rubbed in contact with a surface of the article to be polished, and surface polishing, trimming and the like can be conducted. Moreover, in barrel polishing in a wet system, usually various additives are added to water, depending upon the purposes.

In the polishing method according to the invention, a liquid such as water, alcohol, or the like is added together with the spherical ceramics and the abrasive. The liquid is not particularly limited to the above mentioned water and alcohol. Further, commercially available polishing additive may be added. Furthermore, an amount of the liquid used is not also limited. However, polishing can preferably be conducted when the volume of the liquid is 1~3 times the volume of the spherical ceramics.

The invention will hereunder be described in detail with reference to various embodiments.

EMBODIMENT 1

Figure 8:
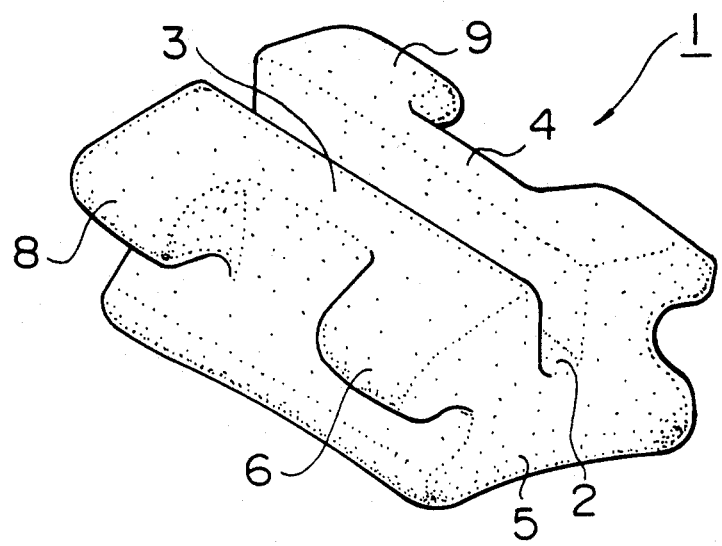
FIG. 8 is a perspective view of a prior-art bracket made of ceramics.
Figure 9:
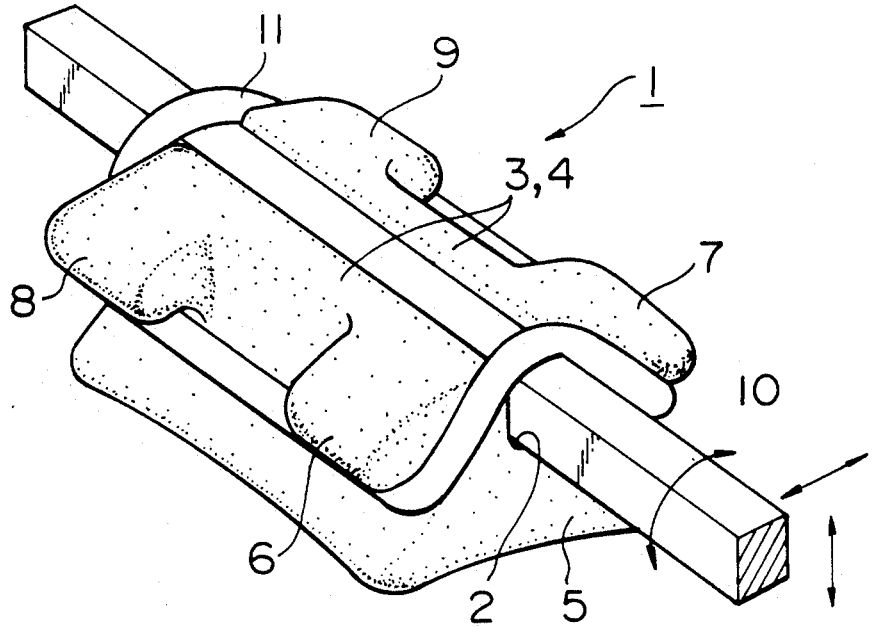
FIG. 9 is a perspective view showing a state at which the bracket illustrated in FIG. 8 is used.

Partially stabilized zirconia (zirconia stabilized with yttria) is selected as a ceramic material. Powder of the partially stabilized zirconia was molded into a bracket configuration by injection molding. The molded zirconia was calcined or baked to remove a binder component contained therein. Subsequently, it was sintered for two (2) hours at 1400° C. to obtain a dental bracket 1 made of zirconia ceramics as illustrated in FIG. 8.

Subsequently, a barrel polishing machine of planetary type was used to conduct polishing under the following conditions.

100 weight parts of truly spherical zirconia beads having a grain size of 200 μm, and 5 weight parts of alumina powder (corresponding to 7.5% of the volume of the zirconia beads) having a mean grain size of 1 μm were placed in a barrel polishing container, and an aqueous solution containing 10% of commercially available barrel polishing additive liquid was added in an amount of about two (2) times the volume of the zirconia beads. The ceramic-made dental bracket 1 as shown in FIG. 8 was placed in the barrel polishing container, and the polishing container was mounted on a barrel polishing machine. The dental bracket 1 was barrel-polished. After having been barrel-polished for approximately ten (10) hours, the dental bracket 1 was taken out of the container, and a roughness of an inner surface of the slot 2 was investigated or examined by the following measuring method.

Figure 2:
FIG. 2 is a photomicrograph, at a high magnification, showing the bottom of the slot in the bracket illustrated in FIG. 1.

A cross-section of the slot 2 and its neighborhood after polished was observed by a scanning electron microscope (SEM) to investigate a roughness on an inner surface of the slot 2. FIGS. 1 and 2 are photographs for a cross-section of the slot 2 which has been polished by the polishing method according to the invention. Specifically, FIG. 1 is a photograph taken at a low magnification, showing the bottom of the slot and its neighborhood, while FIG. 2 is a photograph taken at a high magnification, showing the bottom of the slot. As shown in the photograph of FIG. 2, the roughness ($R_{max}$) on the inner surface of the slot 2 is equal to or less than 2 μm, which shows that the inner surface of the slot is very smooth. Further, any scratch and defect causing lowering of the strength of the dental bracket are not found. As a result, it became possible to reduce the friction of the ceramic-made dental bracket 1 to a value similar to that of a metallic bracket. When the bracket which had been polished in the above mentioned manner was used as a dental bracket, it was possible to shorten a treatment time required for reforming a dental alignment, compared with a treatment time required when a conventional ceramic-made bracket (which has not been polished according to the present invention) is used.

Figure 3:
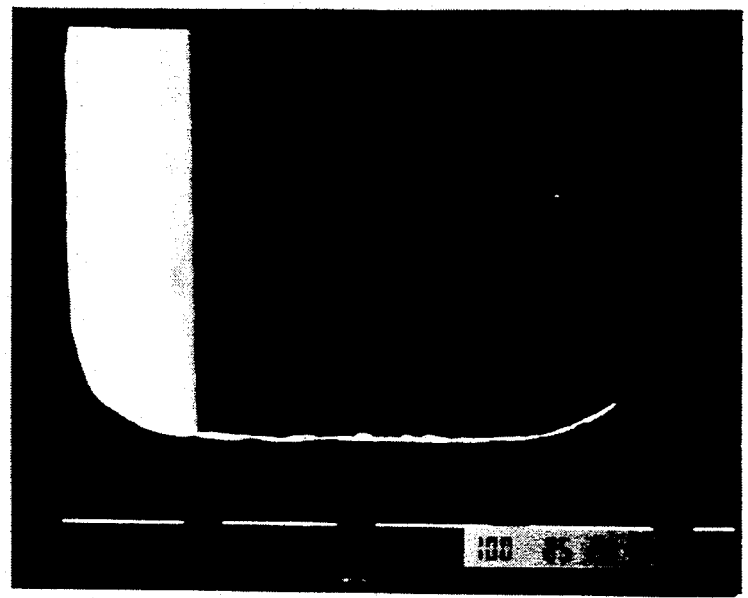
FIG. 3 is a photomicrograph, at a low magnification, showing the bottom of the slot and its neighborhood in the dental bracket prior to polishing, according to the embodiment 1 of the invention.
Figure 4:
FIG. 4 is a photomicrograph, at a high magnification, showing the bottom of the slot in the bracket illustrated in FIG. 3.

FIGS. 3 and 4 show a surface of the slot 2 prior to polishing the above-described dental bracket 1. Specifically, FIG. 3 is a photograph taken at a low magnification, showing the bottom of the slot and its neighborhood, while FIG. 4 is a photograph taken at a high magnification, showing the bottom of the slot. As shown in the photograph of FIG. 4, a number of convexes of about 6 μm at maximum are seen on the surface of the slot. These concaves-convexes are ones which are formed by transfer of concaves-convexes on the inner surface of an injection mold, when the dental bracket is produced.

EMBODIMENT 2

Figure 5:
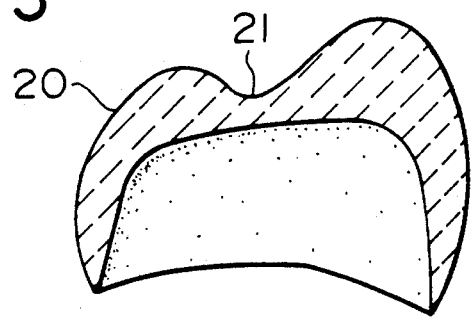
FIG. 5 is a cross-sectional view of an artificial dental crown.

A glass ceramic, an alumina ceramic, a zirconia ceramic, and an apatite ceramic were respectively formed into a dental crown configuration as shown in FIG. 5, to manufacture artificial dental crowns 20. These crowns were polished in a method similar to that of the Embodiment 1, by the use of true spherical zirconia beads whose grain size is 70 µm.

The artificial dental crowns 20 polished show a gloss which resembles a natural tooth, on an outer side and an inner side thereof. A narrow recess 21 at a biting portion of the artificial dental crown 20 has been polished well.

This means that in the artificial dental crowns 20 according to the embodiment, dental plaque is difficult to be deposited thereon, and the strength thereof is also improved.

EMBODIMENT 3

Figure 6:
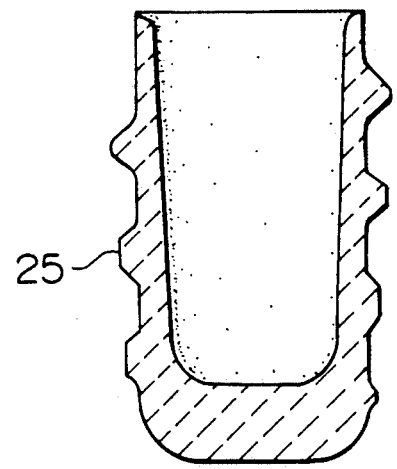
FIG. 6 is a cross-sectional view of a cap for a dental implant.

Bioactive ceramics such as an apatite ceramic, a bioactive glass ceramic or the like is formed into a threaded cap configuration, cross-section of which is shown in FIG. 6. The cap 25 made of ceramics is used as a component of a dental implant. The cap 25 was polished in a same as in the Embodiment 1, except that true spherical zirconia beads having a grain size of 100 µm was used instead of true spherical zirconia beads having a grain size of 200 µm. The cap 25 polished in this method shows a gloss on an outer side and an inner side thereof. Particularly, a root portion of a screw which is located on the outside of the cap was well polished. In the root portion of the screw, stress is liable to be concentrated. By polishing the root portion, the strength of the cap 25 is improved.

EMBODIMENT 4

Figure 7:
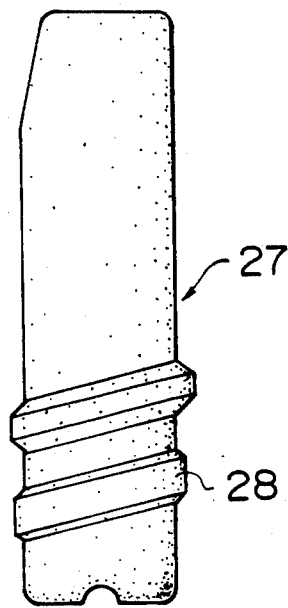
FIG. 7 is a front elevational view of the dental implant.

Bioactive ceramics such as an apatite ceramic, a bioactive glass ceramic or the like is formed into a configuration of a dental implant 27, as shown in FIG. 7. The dental implant 27 was polished in a method similar to that of the Embodiment 3. A threaded portion 28 was well polished like the Embodiment 3, and the strength of the dental implant 27 was improved.

As described above, according to the method of polishing the dental instrument, it is possible to superiorly or reliably polish the surface of the dental instrument having fine irregular portions including narrow grooves or recesses, particularly, the fine irregular portions, which have been difficult by the conventional method. By polishing the surface of the dental instrument, particularly, the fine irregular portions such as grooves or recesses in accordance with the method of the invention to remove defects which cause lowering of strength of the dental instrument, it is possible to reduce variation in strength of products. Further, by polishing the surface, it is possible to reduce deposition of dental plaque and breeding or propagation of various bacteria. Further, in case where the process of the invention is applied to the dental bracket, it is possible to maintain abrasion or wear of the arch wire or the ligature wire to the minimum. Particularly, by polishing the inner surface of the slot, it is possible to reduce the friction between the slot inner surface and the arch wire.

What is claimed is:

1. A method of polishing a dental instrument, selected from the group consisting of an artificial dental crown, a dental implant and a dental bracket, comprising the steps of:

placing, into a container, the dental instrument, spherical ceramics whose grain size is 30~400 µm, an abrasive whose grain size is at most equal to 20 µm and a liquid, said dental instrument being made of a ceramic material, and having fine irregular portions along a surface thereof; and moving said container thereby polishing said dental instrument.

2. A method of polishing a dental instrument, according to claim 1, wherein said irregular portions include narrow grooves and recesses.

3. A method of polishing a dental instrument, according to claim 2, wherein said narrow groove and recess in said dental instrument has a width of 450~500 µm and a depth of 700~900 µm.

4. A method of polishing a dental instrument, according to claim 1, wherein said dental instrument is one selected from the group consisting of an artificial dental crown, a dental implant and a dental bracket.

5. A method of polishing a dental instrument, according to claim 1, wherein a ceramic selected from the group consisting of zirconia, silica, alumina, silicon carbide, and silicon nitride is used as a material for said spherical ceramics.

6. A method of polishing a dental instrument, according to claim 5, wherein said zirconia is partially stabilized zirconia.

7. A method of polishing a dental instrument, according to claim 6, wherein said partially stabilized zirconia is zirconia stabilized with yttria.

8. A method of polishing a dental instrument, according to claim 1, wherein said abrasive is selected from the group consisting of alumina, zirconia, silicon carbide, silicon nitride, cerium oxide and diamond.

9. A method of polishing a dental instrument, according to claim 1, wherein the amount of said abrasive placed in said container is 1~50% based on the volume of said spherical ceramics.

10. A method of polishing a dental instrument, according to claim 1, wherein the amount of said abrasive placed in said container is 1~15% based on the volume of said spherical ceramics.

11. A method of polishing a dental instrument, according to claim 1, wherein the amount of said abrasive placed in said container is 1~8% based on the volume of said spherical ceramics.

12. A method of polishing a dental instrument, according to claim 1, wherein said liquid comprises water or alcohol.

13. A method of polishing a dental instrument, according to claim 1, wherein an amount of the liquid is placed in the container about 1~3 times the volume of said spherical ceramics.

* * * * *